United States Patent
Mihaila

(10) Patent No.: US 7,612,551 B2
(45) Date of Patent: Nov. 3, 2009

(54) SYSTEM OF PHONON SPECTROSCOPY

(75) Inventor: Mihai N. Mihaila, Burcharest (RO)

(73) Assignee: Honeywell International Inc., Morristown, NJ (US)

(*) Notice: Subject to any disclaimer, the term of this patent is extended or adjusted under 35 U.S.C. 154(b) by 147 days.

(21) Appl. No.: 11/779,775

(22) Filed: Jul. 18, 2007

(65) Prior Publication Data

US 2008/0024113 A1    Jan. 31, 2008

Related U.S. Application Data

(60) Provisional application No. 60/832,440, filed on Jul. 21, 2006.

(51) Int. Cl.
  *G01R 23/16* (2006.01)
(52) U.S. Cl. .................. 324/76.19; 324/71.1
(58) Field of Classification Search .......... 324/76.19, 324/71.1
  See application file for complete search history.

(56) References Cited

U.S. PATENT DOCUMENTS

2006/0027021 A1 * 2/2006 Choi et al. .................. 73/579

OTHER PUBLICATIONS

Akimenko et al., "Point-Contact Noise Spectroscopy of Phonons in Metals," Journal of Low Temperature Physics, vol. 54, Nos. 3/4, pp. 247-266, 1984.

Antonov et al., "Point-Contact Spectroscopy of the Electron-Phonon Interaction in Palladium," Journal of Physics: Condensed Matter, vol. 3, No. 33, pp. 6523-6530, Aug. 19, 1991.

Bowmar et al., "Raman and Infrared Determination of Vibrational Fundamentals of Single-Crystal C60 and Derivatives and of C70," Journal of Physics: Condensed Matter 6, pp. 3161-3170, 1994.

Carruthers, "Bias-Dependent Structure in Excess Noise in GaAs Schottky Tunnel Junctions," Applied Physics Letters, vol. 18, No. 1, pp. 35-37, Jan. 1, 1971.

Coulombeau et al., "Inelastic Scattering of Footballene C60," The Journal of Physical Chemistry, vol. 96, No. 1, pp. 22-24, Jan. 9, 1992.

Li et al., "Low-Frequency Noise in Transport Through Quantum Point Contacts," Applied Physics Letters, vol. 57, No. 8, pp. 774-776, Aug. 20, 1990.

Marcus, "Exchange Reactions and Electron Transfer Reactions Including Isotopic Exchange Theory of Oxidation-Reduction Reactions Involving Electron Transfer," Discussions of the Faraday Society, Oxidation-Reduction Reactions in Ionizing Solvents, No. 29, 1960.

Martin et al., "Observation and Assignment of Silent and Higher-Order Vibrations in the Infrared Transmission of C60 Crystals," The American Physical Society, Physical Review B, vol. 50, No. 1, pp. 173-181, Jul. 1, 1994.

(Continued)

*Primary Examiner*—Vincent Q Nguyen
(74) *Attorney, Agent, or Firm*—Kris T. Fredrick

(57) ABSTRACT

A system for phonon spectroscopy for attaining a phonon spectrum of a sample of a material. Current may be injected into the material to result in electrical noise in the material. The electrical noise may be processed to result in information revealing a phonon spectrum of the material. The phonon spectrum may be useful for analyzing and monitoring various features of the material. Other information about the material may be obtained from the electrical noise.

17 Claims, 11 Drawing Sheets

OTHER PUBLICATIONS

Myers, "Resonance Raman Intensities and Charge-Transfer Reorganization Energies," Chemical Reviews, vol. 96, No. 3, pp. 911-926, May 1996.

Mihalia, "1/f Noise Phonon Spectroscopy in INAlAs/InGaAs HEMT's," Proceedings of the 14th International Conference; Noise in Physical Systems and 1/f Fluctuations, pp. 51-54, Jul. 1997.

Mihalia, "Lattice Vibrations in Silicon by 1/f Noise Spectroscopy," Proceedings of the 8th International Conference on 'Noise in Physical Systems' and the 4th International Conference on '1/f Noise' Rome, pp. 433-435, Sep. 9-13, 1985.

Mihalia et al., "Nonlinear Effects in the 1/f Noise of a 2D Electron Gas," IFAC Large Scale Systems: Theory and Applications, pp. 319-324, 2001.

Mihalia et al., "Nonlinear Effects in the 1/f Noise of Lattice-Matched InAlAs/InGaAs HEMT's," Sixth Quantum 1/f Noise and Other Low Frequency Fluctuations in Electronic Devices Symposium, St. Louis Mo., pp. 127-133, May 1994.

Mihalia et al., "Origin of 1/f Noise in InAlAs/InGaAs HEMT's," IPRM '96 Conference Proceedings, pp. 368-371, Apr. 21-25, 1996.

Mihalia, "Phonon Fine Structure in the 1/f Noise of Metals, Semiconductors and Semiconductor Devices," Noise Oscillators and Algebraic Randomness, pp. 217-231, Apr. 5-10, 1999.

Mihalia, Phonon Fingerprints in the 1/f Noise of Discontinuous Platinum Films, Noise in Physical Systems and 1/f Fluctuations, pp. 17-22, 1991.

Mihalia, "Phonon Observations from 1/f Noise Measurements," Physics Letters, pp. 157-158, Aug. 20, 1994.

Mihalia, "Phonon Signatures in the 1/f Noise Parameter of Copper, Silver and Silicon," Physics Letters, vol. 107A, No. 9, pp. 465-467, Mar. 4, 1985.

Mihalia, "Phononic Structures in the 1/f Noise Parameter of The Gold Films," Proceedings of the 8th International Conference on 'Noise in Physical Systems' and the 4th International Conference on '1/f Noise' Rome, pp. 437-439, Sep. 9-13, 1985.

Mihalia et al., "Relaxation Mechanisms in 2D Electron Gas and Origin of 1/f Noise in HEMT's," IEEE Proceedings of 20th International Conference on Microelectronics, (MIEL'95), vol. 1, pp. 447-452, Sep. 12-14, 1995.

Nissen et al., "Highly Structured Singlet Oxygen Photoluminescence from Crystalline C60," The American Physical Society, Physical Review Letters, pp. 2423-2426, Oct. 19, 1992.

Novoselov et al., "Two-Dimensional Gas of Massless Dirac Fermions in Graphene," Nature, vol. 438, pp. 197-200, Nov. 10, 2005.

Phillips et al., "Low-Frequency Noise in Very High Mobility Modulation-Doped Structures," Applied Physics Letters, vol. 61, No. 24, pp. 2926-2928, Dec. 14, 1992.

Pintschovius et al., "Inelastic Neutron Scattering Study of the External Vibrations in Single Crystal C60," The American Physical Society, Physical Review Letters, vol. 69, No. 18, Nov. 2, 1992.

Ralls et al., "Microscopic Study of 1/f Noise in Metal Nanobridges," The American Physical Society, Physical Review B, vol. 44, No. 11, pp. 5800-5817, Sep. 15, 1991.

Saito et al., "Physical Properties of Carbon Nanotubes," Book, to be Supplied When it Becomes Available, 1998.

Yanson et al., "Electrical Fluctuations in Normal Metal Point-Contacts," Solid State Communications, vol. 43, No. 10, pp. 765-768, 1982.

Zhang et al., "Experimental Observation of the Quantum Hall Effect and Berry's Phase in Graphene," Nature, vol. 438, pp. 201-204, Nov. 10, 2005.

Saito et al., "Physical Properties of Carbon Nanotubes," Book previously cited on IDS filed Mar. 20, 2008, 259 pages, 1998.

\* cited by examiner

SYSTEM OF PHONON SPECTROSCOPY

This application claims the benefit of U.S. Provisional Application No. 60/832,440, filed Jul. 21, 2006.

BACKGROUND

The invention pertains to spectroscopy and particularly to phonon spectroscopy.

SUMMARY

The invention is a mechanism and approach for attaining a phonon spectrum of a material from electrical noise.

DESCRIPTION

Figure 1:
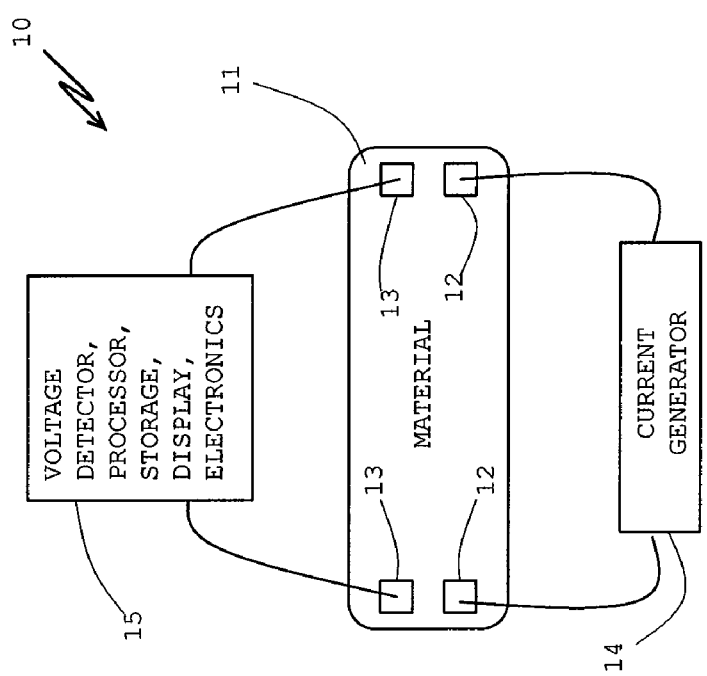
FIG. 1 is a diagram of an example apparatus for facilitating an obtaining a phonon spectrum from electrical noise.

There are various approaches to investigate the atomic vibration spectrum of a solid-state matrix such as Raman spectroscopy, surface enhanced Raman (SER) spectroscopy, infrared (IR) absorption, with Fourier transform of infrared radiation (FTIR) as its variant, electron energy loss spectroscopy (EELS), neutron inelastic scattering (NIS), inelastic electron tunneling spectroscopy (IETS), point contact spectroscopy (PCS) and others. Some of these approaches (INS, EELS) may require sophisticated and expensive equipments. The sensitivity of some approaches is target dependent; therefore, it may be impossible or very difficult to use them for small dimensional systems (e.g., INS, Raman or IR spectroscopy). Many of these approaches may use a monochromatic or continuous tunable source of radiation (Raman, IR, INS, EELS). Some of them may be efficient only at very low temperature and high vacuum (e.g., EELS, IETS, PCS). Special preparation of the sample may be required by some of them (e.g., IETS, PCS). In general, an electrical approach of spectroscopy may be easier to use. However, the existing electrical approaches, namely IETS and PCS, have the drawbacks mentioned herein, and these are the factors which limit the application of them for practical purposes. Both IETS and PCS may rely on the weak variation in the conductance of the investigated sample around the phonon emission thresholds. Another factor, which can be very sensitive to the phonon emission, may be the fluctuations of the conductance or the electrical noise. A purpose here is to disclose an electrical approach of lattice vibration spectroscopy (i.e., phonon spectroscopy), which may rely on the electronic noise measurement.

Electrons flowing in a crystal may suffer both elastic and inelastic scattering. In the inelastic scattering process, the electrons may cease energy to the lattice in form of phonons. Since all inelastic processes are resonant in character, one may expect strong fluctuations in the mobility at or around the phonon emission thresholds. These fluctuations in mobility may produce fluctuations in resistance and, consequently, in the voltage across the resistor terminals. The present approach may address an issue of using electronic noise in a resistor to measure the vibration spectrum of the atoms composing of the material which the resistor is made. To apply the present approach, current may be injected into the resistor terminals and the noise spectrum of the fluctuating voltage (V) developed across the resistor terminals may be measured. The noise intensity, normalized to the squared voltage, $S(f,T)/V^2$, may be plotted as a function of voltage (V) or as a function of its equivalent wavenumber. Usually, $S(f,T)/V^2$ vs. V may feature a fine structure corresponding to the phonon energies of the investigated material. It may be validated by a comparison with data obtained by other approaches.

The electrons flowing in a solid-state matrix may interact both elastically and inelastically with the atoms of the matrix. In the inelastic process, electrons may loose energy in small quantities corresponding to the specific energy of vibration (phonons) of the matrix atoms. The inelastic interaction of the particles with the lattice phonon is fundamental to many methods or approaches of spectroscopy. But inelastic processes are dissipative mechanisms in a solid. Consequently, although not explicitly discussed in the literature, the dissipation seems to be the fundamental principle underlying the approaches of spectroscopies which rely on inelastic scattering of elementary particles (photons, electrons, neutrons) and atoms.

For instance, in both IETS and PCS, a structure in conductance may occur whenever the condition $eV=\omega\omega_{ph}$ is fulfilled (e—elementary charge, V—applied voltage, $\omega$—Planck's constant, $\omega_{ph}$—phonon frequency). In this context, one may note that the relation $eV=\omega\omega_{ph}$ is valid only when the electron energy is dissipated by inelastic interaction of electrons with lattice phonons; therefore, this relation may also be viewed as an expression of the fluctuation-dissipation relation. Although the fluctuation-dissipation relation is strictly valid only in equilibrium, one may suppose that in a resistor very close to equilibrium, a dissipation process would also be accompanied by noise. According to this supposition, whenever a dissipation channel is opened, an increased noise level (noise structure) can occur at voltages corresponding to the phonon energies. Based on this observation one would expect an observation of a fine noise structure in a system (resistor) when it is slightly out of equilibrium.

In fact, such a noise structure was observed in an Au—GaAs Schottky tunnel diode by Carruthers (Bias-Dependent Structure in Excess Noise in GaAs Schottky Tunnel Junctions, Appl. Phys. Lett., 18, 35 (1971)), Yanson et al. (I. K. Yanson, A. I. Akimenko and A. B. Verkin, Electrical fluctuations in normal metal point-contacts, Solid-St. Commun. 43, 765 (1982)), and Akimenko et al. (A. I. Akimenko, A. B. Verkin, and I. K. Yanson, Point-Contact Noise Spectroscopy of Phonons in Metals, J. Low Temperature Physics 54, 247 (1984)) in metallic point contacts. In these cases, noise peaks were observed at voltages corresponding to phonon energies. Moreover, Akimenko observed that the noise peaks are due to Umklapp phonons (phonons involving reciprocal lattice wave vectors). Such observation may point to a connection between noise and the dissipation mechanisms.

One may consider a resistor of a few microns in length and some resistance R. If the resistor is in a thermal equilibrium, there is no dissipation. One may now suppose that the resistor is slightly driven out from equilibrium by injecting excess carriers so as a voltage (V) develops across the resistor terminals. If the voltage is varied from a few millivolts (mV) to a few tens of mV (of the order of phonon energies), then one may expect a sequential opening of the dissipation channels, where an electron dissipates its energy (eV) by creating a non-equilibrium phonon of energy $\omega\omega_{ph}$. However, in a trivial resistor, an electron cannot acquire an energy eV by tunneling or ballistic motion, because these phenomena are not possible. However, an electron can acquire an energy eV if it is diffusing from one terminal to another of the resistor. In the diffusion regime, an electron can suffer only elastic scattering. It can happen if the electric field is small and, consequently, the drift velocity is very small in comparison with the thermal velocity of the electron. The electrons diffusing between the resistor terminals suffer elastic collisions and, consequently, at least in principle, an electron can have a kinetic energy eV when it reaches the second terminal. A similar situation can occur in a granular (nanoparticle) resistor but in this case the electron can suffer elastic tunneling between the grains. If this energy equals the energy of a phonon mode, $eV = \omega\omega_{ph}$, the electron can dissipate its energy by creating a nonequilibrium phonon. Therefore, a noise peak would appear whenever this condition is fulfilled. In the present approach, excess carriers may be injected into the sample. It may justify the hypothesis that, along with a drift component, a diffusion component could also exit the sample.

Another possible explanation that the present approach could rely on, may be found in the Marcus electron transfer theory (R. Marcus, Disc. Faraday Soc. 29, 21, 1960). Most of the results presented in the present approach were obtained by investigating carbonic nanoparticle films containing traces of C60 and C70 fullerenes molecules embedded in a graphite matrix.

Some of the electrons injected into the nanoparticle film may be transferred at the interface between graphite matrix and C60 molecules. In terms of the Marcus theory, any process of electron transfer may be accompanied by energy reorganization at the interface. When a system undergoes a charge transfer, the equilibrium position of the nuclei may change. Consequently, the atoms of both the molecule and matrix may move to reach the equilibrium configuration of the reactant states while staying in the potential energy well of the product state. (Anne B. Myers, Chemical Reviews 96, 911, 1996.)

In other words, very small atomic motion or phonons are participating in the energy reorganization at the interface between the C60 molecule and graphite. Such infinitesimal motions of the atoms in molecule may be felt as fluctuations in the conductivity of the sample and, consequently, in the noise. A phonon fine structure corresponding to the specific vibration modes of the molecule is expected in the noise of the material. This would be a phenomenological basis of the present approach.

FIG. 1 is a diagram showing an illustrative example of an apparatus 10 which may be used to implement the present approach. In order to apply the present approach to do phonon spectroscopy in a given material 11, one may prepare a sample or a matrix of this material 11. In essence, such a sample or material 11 may be a resistor 11 with two, four or more terminals 12 and 13. The sample or resistor 11 may be configured with different terminals, the most usual being those with two or four terminals. In the latter case, two terminals 12 may be used for current injection, while a voltage develops across the other two terminals 13.

In applying the present approach, a current generator 14 may be used to inject current in the investigated resistor 11. Current pulses or incremental current steps may be used to bias the sample or resistor 11 at a given fluctuating voltage (V) with an average value V. Current pulses of different amplitudes may be injected to terminals 12 so as to obtain an increased voltage across the sample 11. For each voltage V, one may use a classical procedure to measure noise in a resistor 11. The voltage (V) developed across the terminals 13 may be amplified and then Fourier transformed by electronics 15. In this way, the voltage noise spectrum ($S_V$) may be obtained. Electronics 15 may contain a voltage detector, a processor, storage, a display, and so forth, to detect, amplify, process, Fourier transform and display signal results, among other things.

To apply the present approach, it is fundamental that the shape of the spectrum to be 1/f or 1/f-like, where f is the frequency of the measurement. Another condition to apply with the present approach is for the investigated sample 11 (resistor) to be linear, therefore the applicability or validity of Ohm's law is needed. Under these circumstances, the noise intensity ($S_V$) at a certain or given frequency may then be normalized ($S_V/V^2$) by A squared voltage ($V^2$) and plotted as a function of voltage (V). A fine structure should be found in the plot of $S_V/V^2$ vs. voltage V. This methodology to apply the present approach should be valid for the embodiments presented herein.

Figure 2:
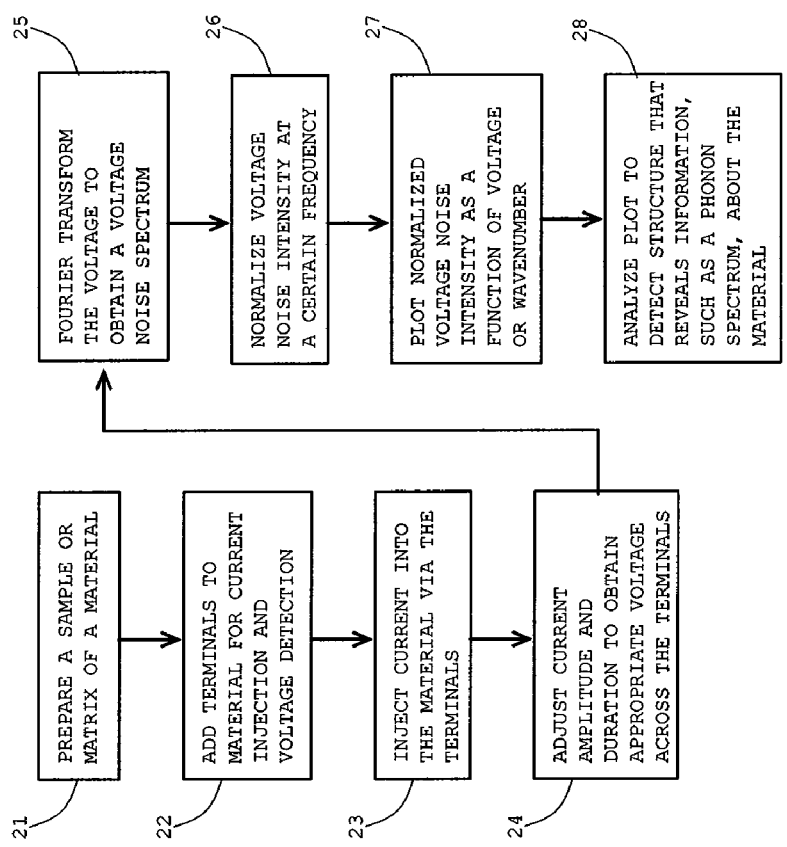
FIG. 2 is a flow diagram of an example approach for attaining a phonon spectrum from electrical noise of a material.

FIG. 2 is a diagram of an illustrative example of the present approach. There may also be variations of the approach shown in FIG. 2. A first step 21 may be to prepare a sample or matrix of a material to be investigated. A second step 22 may be to add terminals to the material for current injection and voltage detection. A third step 23 may be to inject current into the material via the terminals. A fourth step 24 may be to adjust current amplitude and duration to obtain an appropriate voltage detected across the terminals for an investigation of the material. A fifth step 25 may be to Fourier transform the voltage to obtain a voltage noise spectrum. A sixth step 26 may be to normalize voltage noise intensity at given or certain frequency. A seventh step 27 may be to plot the normalized noise intensity as a function of voltage. An eighth step 28 may be to analyze the plot to detect a structure that reveals information about the material.

In a first embodiment, the noise may be measured in a system whose properties are governed by 3D transport of the carriers (bulk samples). Any solid-state conductive material can be used to this purpose. This material may be a metal, semiconductor, alloy, different combinations between different materials obtained by different technological methods or approaches. Bulk, surface and interface properties may be monitored by the present approach. The present approach may be applied to monitor the modifications (including functionalization) of the properties of the materials under the influence of the physical, chemical, biological factors, and so on.

In another embodiment, the noise may be measured on systems whose properties are governed by two-dimensional transport (2D) of the carriers (e.g., surfaces, interfaces). The present approach may be used to investigate the properties of these systems and to monitor the modification of their properties by physical, chemical or biological methods or approaches. Moreover, any surface modification, including those induced by its functionalization, may be monitored.

In another embodiment, the noise may be measured in systems whose properties are governed by unidimensional (1D) transport of the carriers, such as, for instance, quantum wires, including carbon nanotubes. The present approach may be used to investigate the properties of these systems and to monitor the modification of their properties by physical, chemical or biological methods or approaches. Moreover, any modification of the 1D system, including those induced by its functionalization, may be monitored.

In yet another embodiment, the properties of a 0D system (e.g., a quantum dot) may be investigated by the present approach. The approach may be used to monitor the modification of the system's properties by physical, chemical or biological methods or approaches. Moreover, any modification of the 1D system, including those induced by its functionalization, may be monitored.

In another embodiment, the present approach may be used to investigate materials located in a nanogap such as a few molecules or a single molecule, regardless of their or its nature, respectively. The effect of another molecule or other molecules on the molecule in the gap may be investigated and monitored by the present approach.

To provide the present approach and apparatus, one may prepare a matrix, in fact, a two or more terminal resistor. The properties of the resistor (matrix) to be investigated may be determined by the transport of the carriers. Consequently, the present embodiments may be defined according to this classification.

To use the present approach, one may do noise measurements on different structures noted as various embodiments. Often, for noise measurements, a battery in series with a low noise resistor may be used to inject current in the terminal of the sample of interest. In the present approach, instead of a battery in series with a low noise resistor, one may use a very low noise current generator (e.g., a Keithley™ 6430). A reason is that resolution of 1 mV or less than 1 mV may be a requirement in the present approach and the use of a battery in series with a resistor does not appear suitable for such a resolution. Another reason is that one needs noise measurements at voltages ranging from few mV to hundreds of mV. Obtaining such a low voltage level and a large voltage range is very difficult to obtain by the classical bias. Current may be injected in pulses of different amplitudes, separated by time intervals, or in the form of a staircase. The pulse length and the time interval between two successive pulses may be variable. When current is injected into the film/substrate, a fluctuating voltage (V) may develop across the film terminals. The voltage may be amplified and then fast Fourier transformed (FFT). What can be obtained is the frequency distribution of the noise signal or voltage noise spectrum. In this way, one may check whether the noise spectrum is 1/f-like. To the final purpose, one may need only the noise intensity ($S_V$) at a given frequency (f). Often, for a linear resistor (Ohm's law being valid), the noise intensity may be a quadratic function of voltage, $S_V \sim V^2$. After the noise measurement, the noise intensity may be represented as a function of voltage. To eliminate the effect of the current, one may work with normalized values of the noise intensity, $S_V/V^2$. Finally, $S_V/V^2$ may be plotted as a function of voltage (V). A dependence of the form $S_V \sim V^2$ may express the validity of the Ohm's law in the domain of noise. If only a linear effect would exist in the generation of noise, then $S_V/V^2$ vs. V would be a constant. According to the present concept, at some given voltages, the noise intensity may feature local deviations from the $V^2$ law. These deviations should manifest as a fine structure consisting mainly of sharp peaks. These peaks could correspond to the vibration spectrum of the material used to prepare the investigated resistor.

As an illustration of the first embodiment, noise measurements were done on two-terminal resistors (samples) prepared from different nanomaterials, i.e., carbonic nanoparticles with a C60 and C70 fullerenic component. The traces of C60 and C70 were observed as a very small, wavy structure in the Raman spectrum of the material used to prepare the resistors for noise measurements. To this purpose, two terminal resistors were prepared from this material. Silicon-silicon dioxide ($Si/SiO_2$) was used as a substrate. Cr/Au contacts were predeposited on $Si/SiO_2$ substrate, with a gap of about 5.5 micrometers between the two contacts. The resistor was realized between the two contacts. Current was injected into the resistor. The voltage developed across its terminals was amplified and fast Fourier transformed (FFT). The measurements were done at room temperature. The noise intensity ($S_V$) at a given frequency (usually, 10 Hz) was normalized $S_V/V^2$ and represented as a function of voltage (V). To facilitate the comparison with other existing data, the voltage (in mV) was converted into an equivalent wave number (1 meV× 8.06 $cm^{-1}$).

Figure 3:
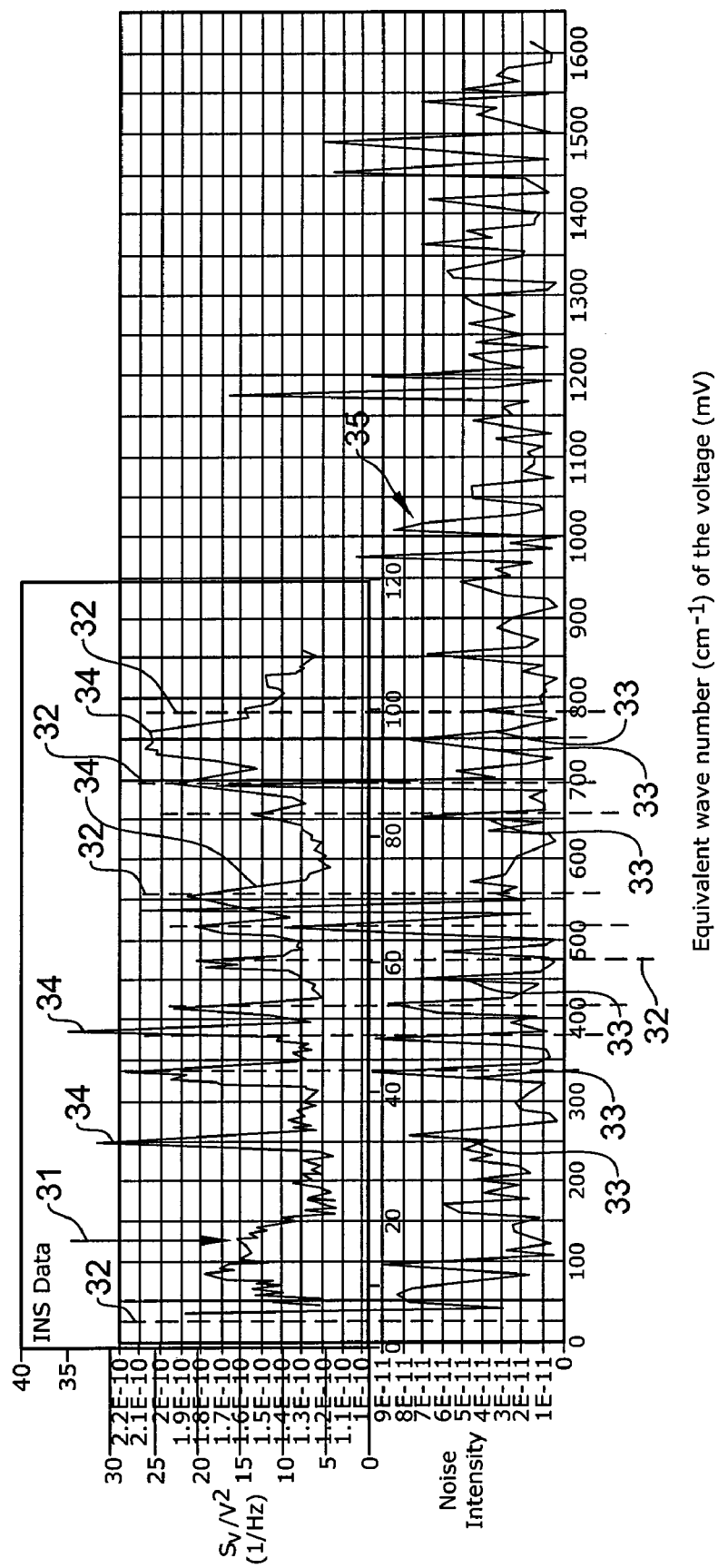
FIG. 3 is a graph showing a comparison between noise intensity versus an equivalent wave number measured at room temperature in a sample containing C60 and C70 fullerenes and data of C60 obtained by inelastic neutron scattering.

FIG. 3 is a graph showing a comparison between $S_V/V^2$ vs. an equivalent wave number measured at room temperature (pulse length-5 seconds, 0.2 Hz, single spectrum) in a sample containing C60 and C70 fullerenes and the spectrum or data 31 of C60 obtained by inelastic neutron scattering (INS), at 25° K (from Coulombeau et al., J. Phys. Chem. 1992, 96, 22-24). Vertical lines 32 may connect the noise peaks 33 with the C60 INS phonon peaks 34. A correspondence between the noise peaks 33 and the INS spectrum 31 of C60 may be observed.

FIG. 3 shows a dependence of the normalized noise spectral density, $S_V/V^2$ vs. equivalent wave number (1 meV×8.06 $cm^{-1}$) for a two-terminal resistor, prepared from carbonic nanoparticles with a fullerenic component. The equivalent wave number, in $cm^{-1}$, may be obtained by multiplication of the voltage with 8.06 $cm^{-1}$, which is the wave number equivalent of 1 meV (1 meV=8.06 $cm^{-1}$). In FIG. 3, $S_V/V^2$ vs. voltage equivalent wave number features a very fine, complex structure, consisting mainly of peaks 33. The structure observed in this sample appears very complicated because of the C60 and C70 molecules existing in the nanomaterial. For instance, the vibration spectrum of a C60 molecule has 174 phonon modes, with 128 of these being degenerate. This structure may be attributed to the electron-phonon interaction. To validate this hypothesis, the $S_V/V^2$ vs. V data were compared with the vibration spectra of graphite, C60 and C70 fullerenes, obtained by different kinds of spectroscopy such as inelastic neutron scattering (INS) spectroscopy, photoluminescence, Raman and infrared spectroscopy. FIG. 3 shows that when compared with the INS data 31 for C60 fullerene (wherein an INS spectrum of C60 measured at 25° K was taken from Coulombeau et al., J. of Chemical Physics 96, 22 (1992)), a good correspondence between the noise data 35 and INS spectrum 31 may be observed to about 800 cm–1.

Figure 4:
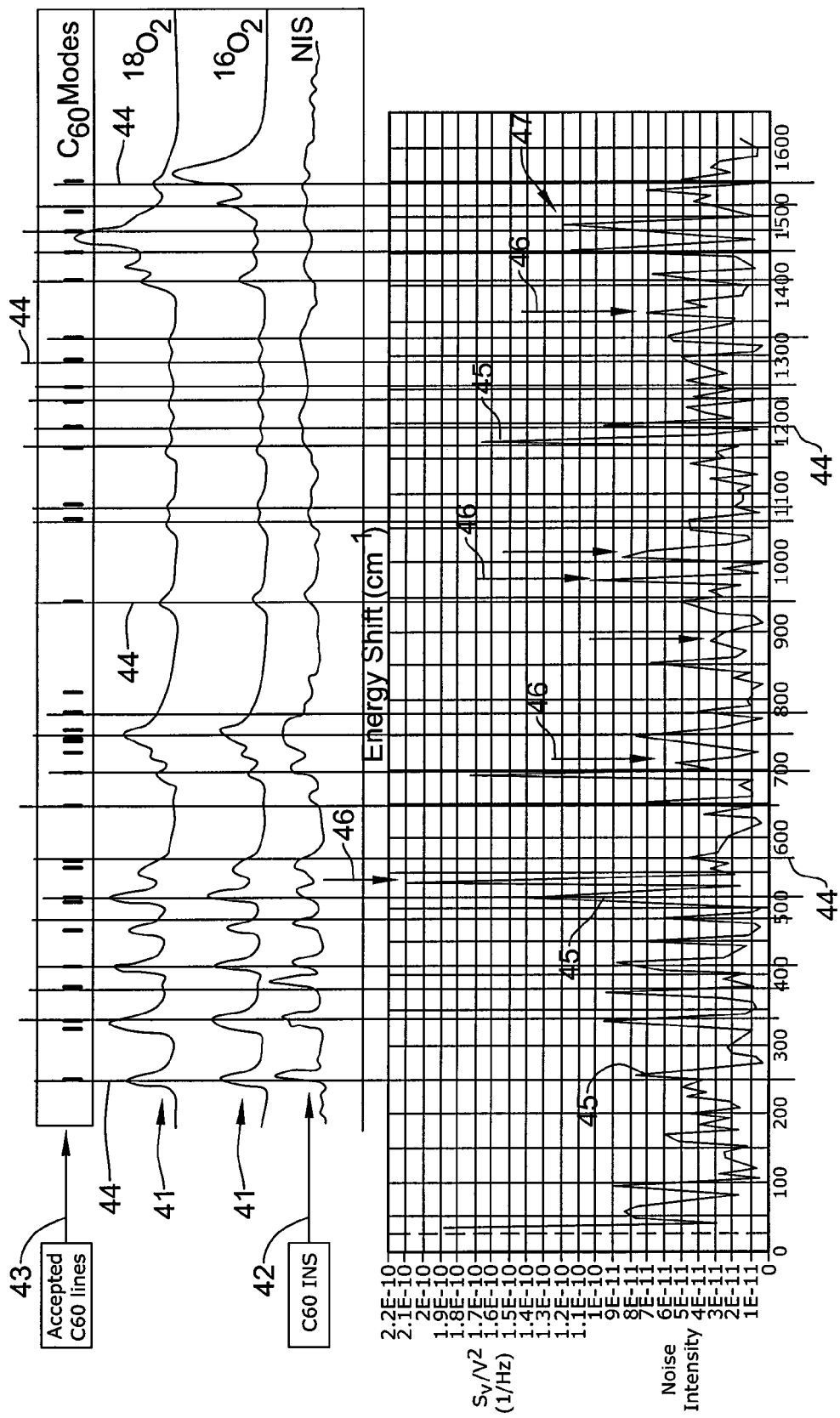
FIG. 4 is a graph showing a comparison between noise intensity versus equivalent wave number and photoluminescence spectrums of C60 with different oxygen content.

FIG. 4 shows a comparison between $S_V/V^2$ vs. equivalent wave number and photoluminescence spectra 41 of C60 with different oxygen content (from Nissen et al., PRL 69, 2423, 1992); also, an NIS spectrum 42 of C60, and C60 lines 43 are figured. Vertical lines 44 may connect the noise peaks 45 with C60 photoluminescence spectrums 41. Good correspondence is observed between the noise peaks 45 and other C60 spectra 41 and 42. The downward oriented arrows 46 indicate noise lines that do not fit the C60 lines.

In FIG. 4, the same noise data 35 from FIG. 3 may be compared with the photoluminescence spectra 41 of C60 (data taken from Nissen et al.). A good correlation may be found between the noise data 47 and the position of the C60 lines 43 in the wave number domain from 250 $cm^{-1}$ to about 1600 $cm^{-1}$.

Figure 5:
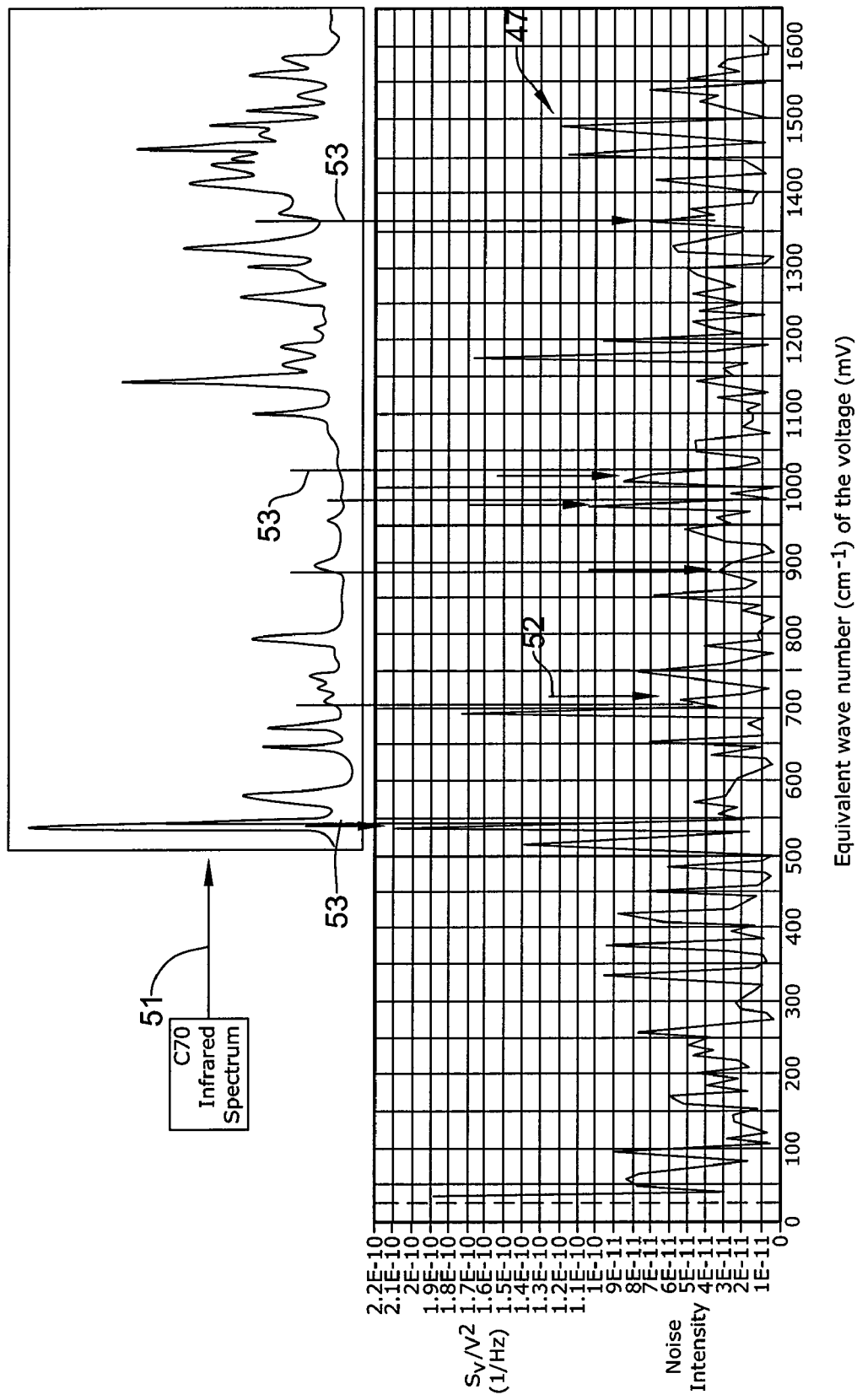
FIG. 5 is a graph showing a comparison of noise data and the infrared spectrum of C70 fullerene.

However, some lines (indicated by downward oriented arrows 46 in FIG. 4) do not appear to fit the C60 lines. Consequently, further comparison was made between these noise data 47 and the infrared spectrum 51 of C70 fullerene. This comparison is shown in FIG. 5. The infrared spectrum 51 of C70 is that of Bowman et al. (J. Phys. Cond. Matter C: 6, 3141 (1994)). The lines 53 indicated by arrows 52 in FIG. 5 may fit the C70 vibration lines. These results strongly support the present approach.

FIG. 5 shows the comparison between $S_V/V^2$ vs. equivalent wave number and infrared spectrum 51 of C70 (data from Bowman et al.). The downward oriented arrows 52 indicate (unidentified) noise lines 53 that do not fit C60 lines. Good correspondence may be observed between the unidentified noise peaks 47 and some C70 vibration lines.

Figure 6:
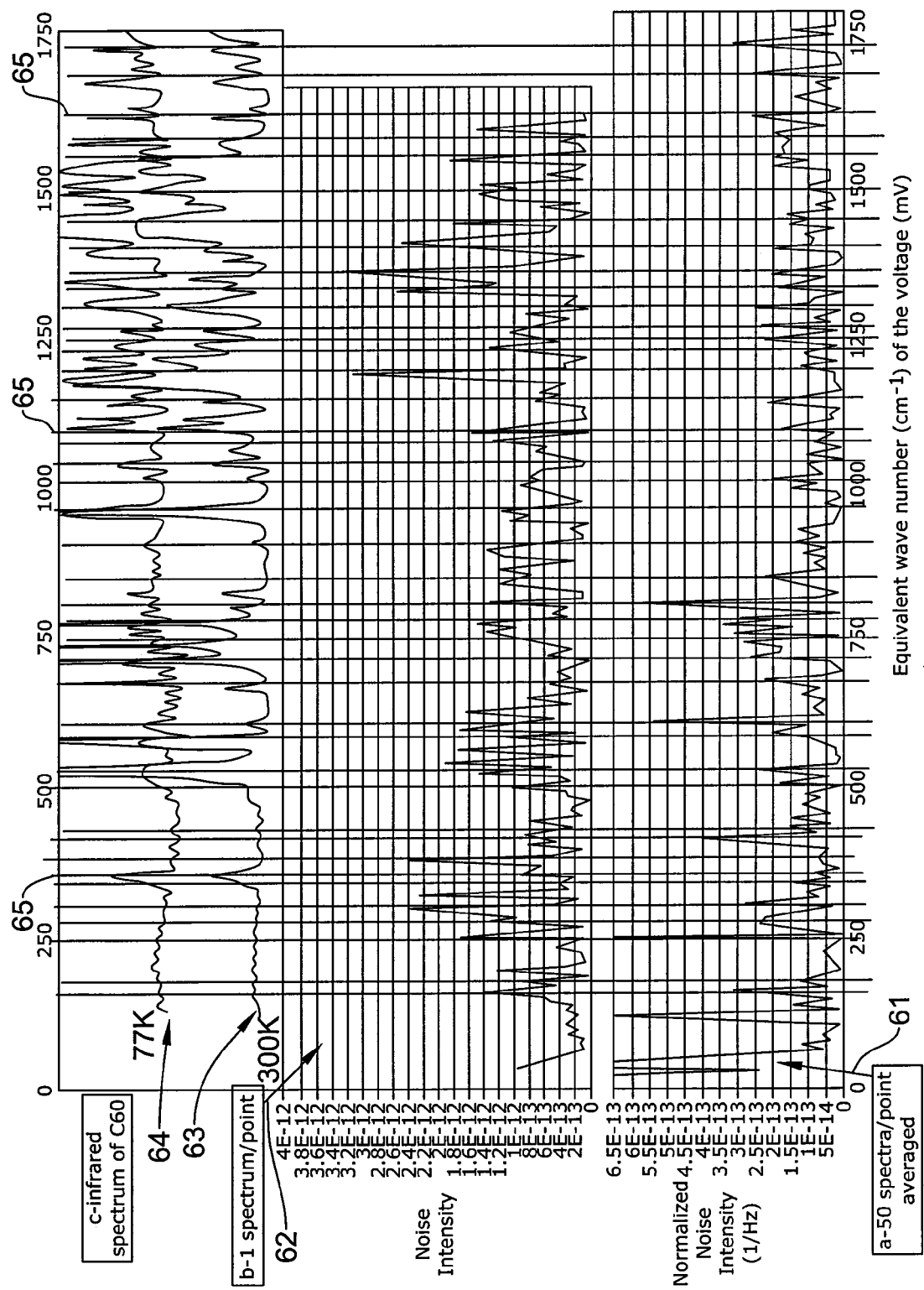
FIG. 6 is a graph showing a comparison between noise intensity versus an equivalent wave number obtained in different measurement runs and the infrared spectrum of C60.

FIG. 6 is a graph showing a comparison between $S_V/V^2$ vs. equivalent wave number obtained in two different measurement runs: a) slow scanning 61 of the sample (50 spectra/point averaged); and b) fast scanning 62 of the sample (1 spectrum/point, pulse length 100 ms, f=10 Hz). A spectrum was obtained at interval of a few months. Both spectra 61 and 62 may be compared with infrared transmission spectra 63 and 64 of C60 single crystal, obtained at 300° K and 77° K, respectively (data from Martin et al., Phys. Rev. B50, 173, 1994-I). The vertical lines 65 evidence a good correspondence between the noise structures observed in the two different runs. Also, in many of the cases, there is a (very) good correlation between the noise peaks and the infrared spectrum 63 and 64 of C60. Few noise peaks that do not correlate are in good correlation with some C70 spectral lines.

For reproducibility purposes, the same sample was measured at intervals of six months. FIG. 6 shows a comparison of the noise data obtained in two different runs and a comparison of both of them with the infrared spectrum of C60. The first run was done with a pulse length of 100 milliseconds, and the sample was scanned fastly (only a spectrum per point was taken). The second run (after six months) was done with a pulse length of 1 second and the sample was slowly scanned (50 spectra were averaged for each biasing point). The infrared spectrum of C60 was taken from Martin et al.). Although the shape of the curve appears quite different, there is a good correlation between the positions of the noise peaks observed at considerable interval of time. Also, a good correlation was found with the infrared spectrum of C60.

In another embodiment, the noise may be measured on systems whose properties are governed by a two-dimensional transport (2D) of the carriers (e.g., surfaces, interfaces). The present approach may be used to investigate the properties of these systems and to monitor the modification of their properties by physical, chemical or biological methods, approaches and factors. The approach may be suitable to characterize the surface properties of any conductive physical system entailing a two dimensional electron gas. In this respect, the approach appears suitable to investigate and characterize the properties of any surface and interface. To this purpose, one may use the four-contact technique—two terminals to inject current and the other two to read and do a spectral analysis of the voltage. One application may be in the investigating of the properties of atomic layers or in a monitoring of an atomic layer deposition technology. Another application may be in the characterization of single graphite layer (graphene) whose properties are governed by the presence of very high mobility (massless or relativistic electrons) (Novoselov et al., Nature, 438, 197, 2005; Zhang et al., Nature 438, 201, 2005). Moreover, any surface modification by physical, chemical, biological methods or approaches, including those induced by its functionalization, or under the presence of adsorbates, may be characterized and monitored by the present approach.

Figure 7:
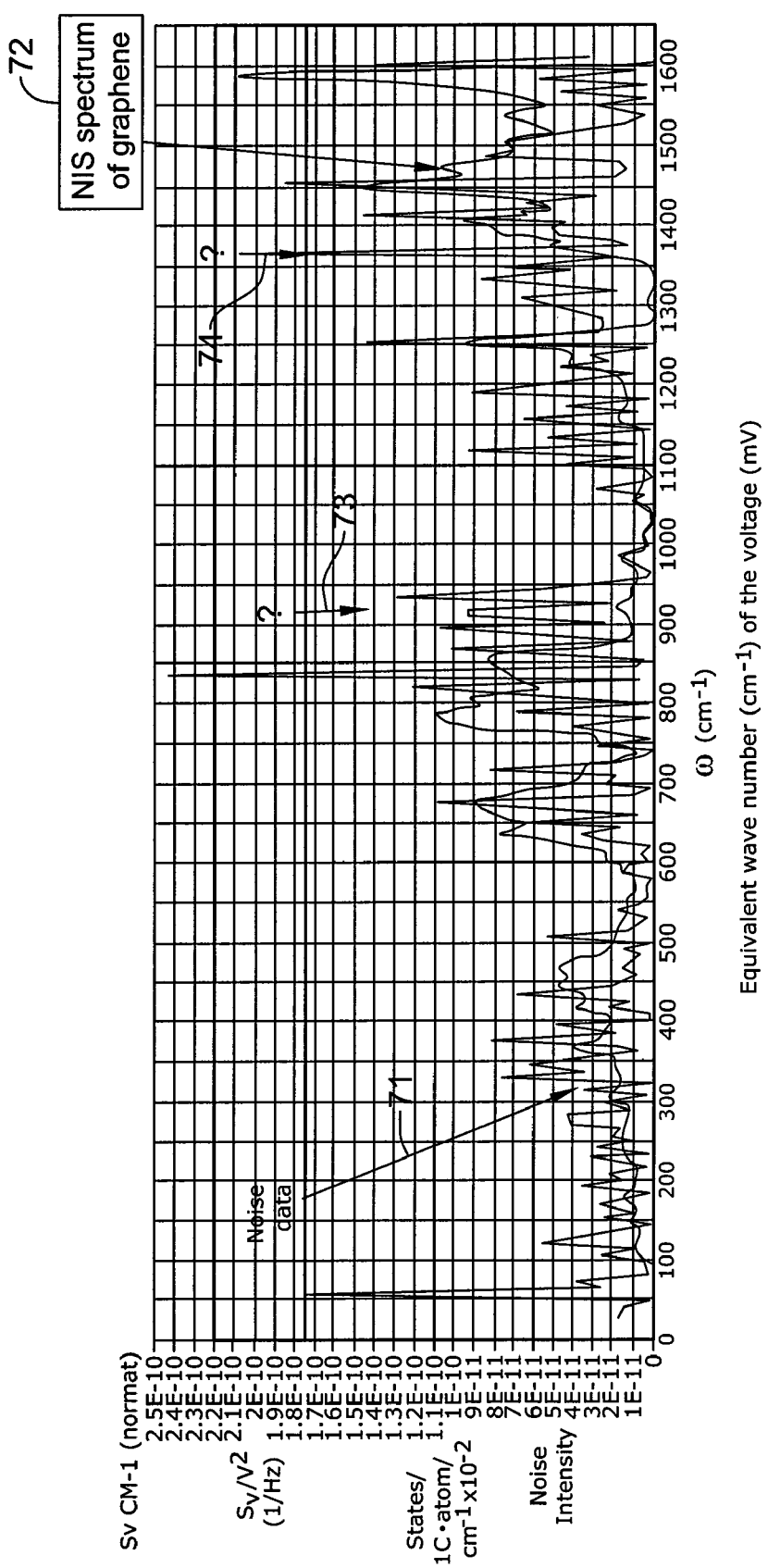
FIG. 7 is a graph showing a comparison between noise intensity versus equivalent wavenumber for a film of an Fe nanoparticle embedded in graphene and the vibration spectrum of graphene.

FIG. 7 is a graph showing a comparison between $S_V/V^2$ (1/Hz) vs. equivalent wavenumber for a film of Fe nanoparticle embedded in a few graphite layers (graphene) and the vibration (phonon) spectrum of 2D graphite (graphene). The graphene spectrum, obtained by neutron inelastic scattering (NIS, Saito et al., Physical Properties of Carbon Nanotubes, London: Imperial College Press, 1998), may be represented along with the phonon spectrum of a carbon nanotube (as it appeared in the cited work of Saito et al.). Some extra-lines (indicated with arrows and "?") are also observed.

As an illustration of this embodiment, FIG. 7 shows a noise measurement 71 done on a film (resistor) of iron nanoparticles embedded in a few layers of graphite (graphene sheets). Iron nanoparticles with the diameter of about 6 nm were used to realize this resistor between two predeposited gold contacts, on a $SiO_2$/Si substrate. The gap between the two contacts was of about 5.5 micrometers. For noise measurements, current was injected into the resistor terminals and the voltage developed across the resistor terminals was amplified and then fast Fourier transformed. The measurements were done at room temperature. FIG. 7 shows a dependence of the normalized 1/f noise intensity ($S_V/V^2$) on voltage equivalent wave number. The $S_V/V^2$ may feature a very fine, complex structure, consisting mainly of peaks along with some "depressions" in the noise intensity. To explain this, the noise vs. voltage may be compared with the phonon density of states (PDOS) 72 of graphene and, determined by inelastic neutron scattering (Saito et al.). To compare the noise data 71 with the graphene PDOS 72, the voltage axis was converted into the wave numbers. When the two x-scales were fitted, a reasonable agreement between the two curves was found. However, some extra-lines appeared. The two downward oriented arrows 73 and 74 indicate a region and, respectively, lines which are in this category. The line located (74) at about 1360 $cm^{-1}$ seems to correspond to the vibrational D band of graphite but a contribution from an impurity is not excluded. The three lines (73) located between (900-950) $cm^{-1}$, could correspond to the vibration lines of some reaction byproducts occurred during the synthesis of the nanomaterial. The example presented indicates that the transport properties in this nanomaterial may be dominated by the properties of the graphene layers in which the iron nanoparticles are embedded.

In another embodiment, noise may be measured on systems whose properties are governed by one-dimensional transport (1D) of the carriers. In this embodiment, the present approach may be used to investigate the properties of quantum wires, regardless of their nature and technology used to fabricate them.

The present approach may also be envisioned to monitor the modification of the quantum wire phonon spectrum induced by physical, chemical or biological methods, approaches and factors, including those produced by functionalization. Individually contacted carbon nanotubes (CNT) may be representative for this embodiment. The present approach may be used to monitor a modification of a contacted carbon nanotube produced by physical, chemical and biological methods or approaches, including those aiming at creation of p-n junctions, heterojunctions or any other functionalization. Also, the present approach may be applicable in the case when the nanotube is biased by electron beams.

Figure 8:
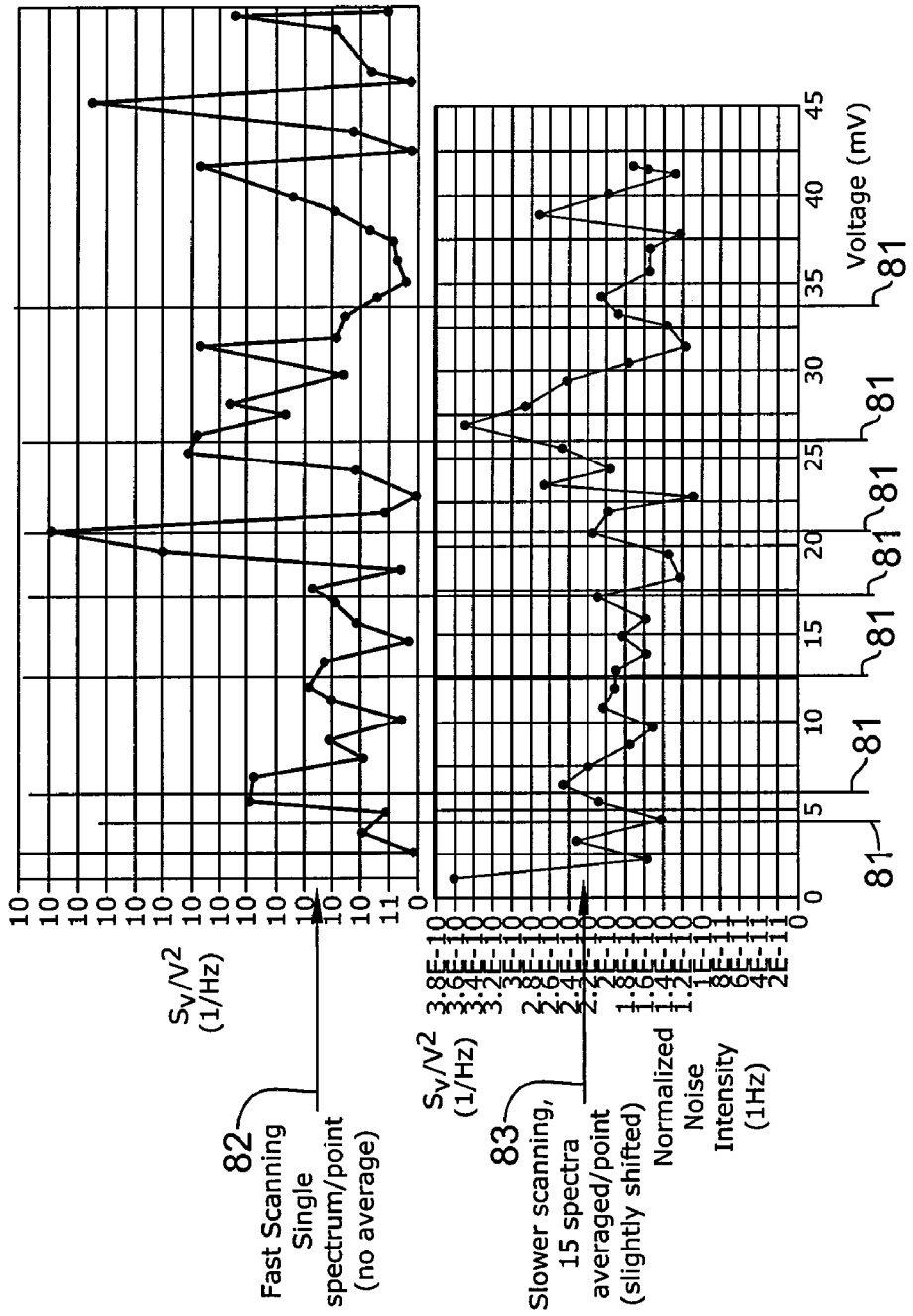
FIG. 8 is a graph showing a comparison between noise data versus voltage obtained in a platinum-carbon nanotube contact for two different measurement runs of in different conditions.

FIG. 8 is a graph showing a comparison between the noise data (the normalized noise intensity, $S_V/V^2$) vs. voltage (V) obtained in two different measurement runs, in different conditions; the vertical lines 81 indicate the correspondence between the noise structures. A good reproducibility is observed. The two scales were slightly shifted.

As an illustration of this embodiment, FIG. 8 shows a noise measurement done on an individual carbon nanotube contacted with palladium (Pd). FIG. 8 shows noise data obtained in two different noise measurement runs. One run 82 was obtained using a single spectrum/point while another run 83 was obtained by averaging 15 noise spectra/points. In both cases, $S_V/V^2$ vs. voltage (V) appears to feature a fine structure, consisting of peaks. As FIG. 8 shows, the noise structure obtained in the two measurement runs compare well, which indicates that the present approach may give reproducible results. The resistance of this Pd contacted CNT was of about 48 k ohms. The CNT length between the two Pd contacts was of about 2 micrometers; therefore, one may assume that the transport in a nanotube is ballistic. Consequently, Pd contact resistance may dominate the total resistance. This is the reason why in FIG. 9 the noise structure 92 in Pd contacted CNT is compared with the Eliashberg function $\alpha 2F(\omega)$ 93, where w is the atomic vibration frequency, of palladium point contact. This function $\alpha 2F(\omega)$ was determined from experimental data for Pd point contact by Antonov et al. (J. Phys.: Condens. Matter 3, 6523, 1991.) The function $\alpha 2F(\omega)$ stands for the function of phonon density of states (PDOS) which takes into account of the topology of palladium Fermi surface. One may note that there appears a significant correspondence between the noise structure observed in both noise measurement 92 runs and the structure 93 in $\alpha 2F(\omega)$. Therefore, the structure observed in the Pd contacted CNT appears due to the Pd contact. Consequently, the present approach may be used to characterize nanocontacts. In general, it can be used to characterize small systems at a nanoscale; therefore, the present approach may be useful for nanoanalysis.

Figure 9:
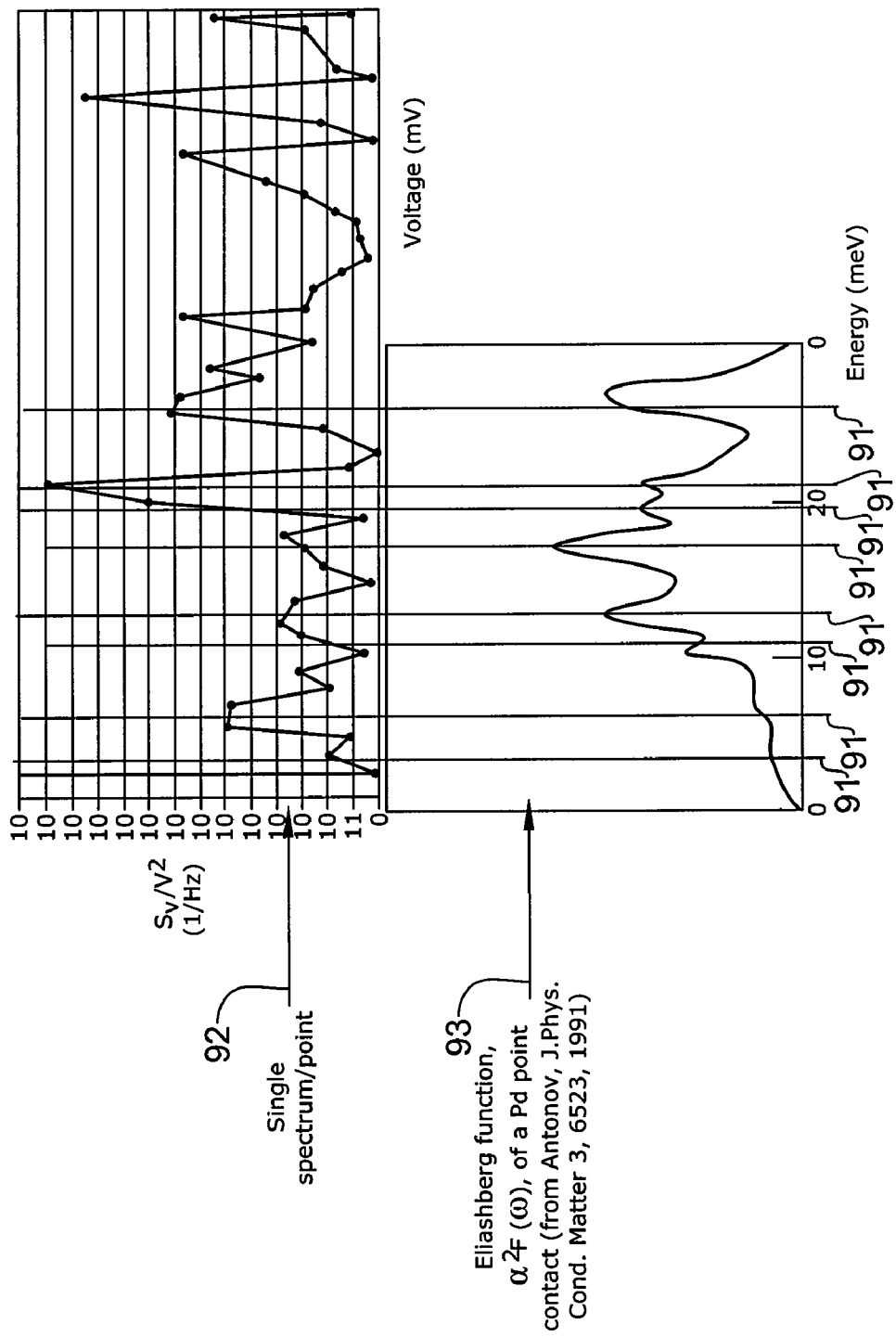
FIG. 9 is a graph showing a comparison between noise intensity versus voltage and the Eliashberg function for the same platinum-carbon nanotube contact used in FIG. 8.

FIG. 9 is a graph showing a comparison between $S_V/V^2$ vs. voltage 92 and the Eliashberg function 93 (product between the phonon density of states, $F(\omega)$, and the electron-phonon matrix element, $\alpha^2$) of a Pd point contact. The data for Pd point contact were obtained at 4.2° K by Antonov et al. The vertical lines 91 indicate a correspondence between the noise structure 92 and the function $\alpha 2F(\omega)$ 93 of Pd.

Noise measurements were done on the sample 11 at low voltage, generally bellow 12 mV, and for different pulse lengths. The measurements were repeated at intervals of days for more than one month. The purpose of the measurements is to look for reproducibility of the noise spectrum, especially the positions of the noise peaks. The noise data were compared with the external molecular spectrum of C60, also known as a libronic vibration spectrum.

Figure 10:
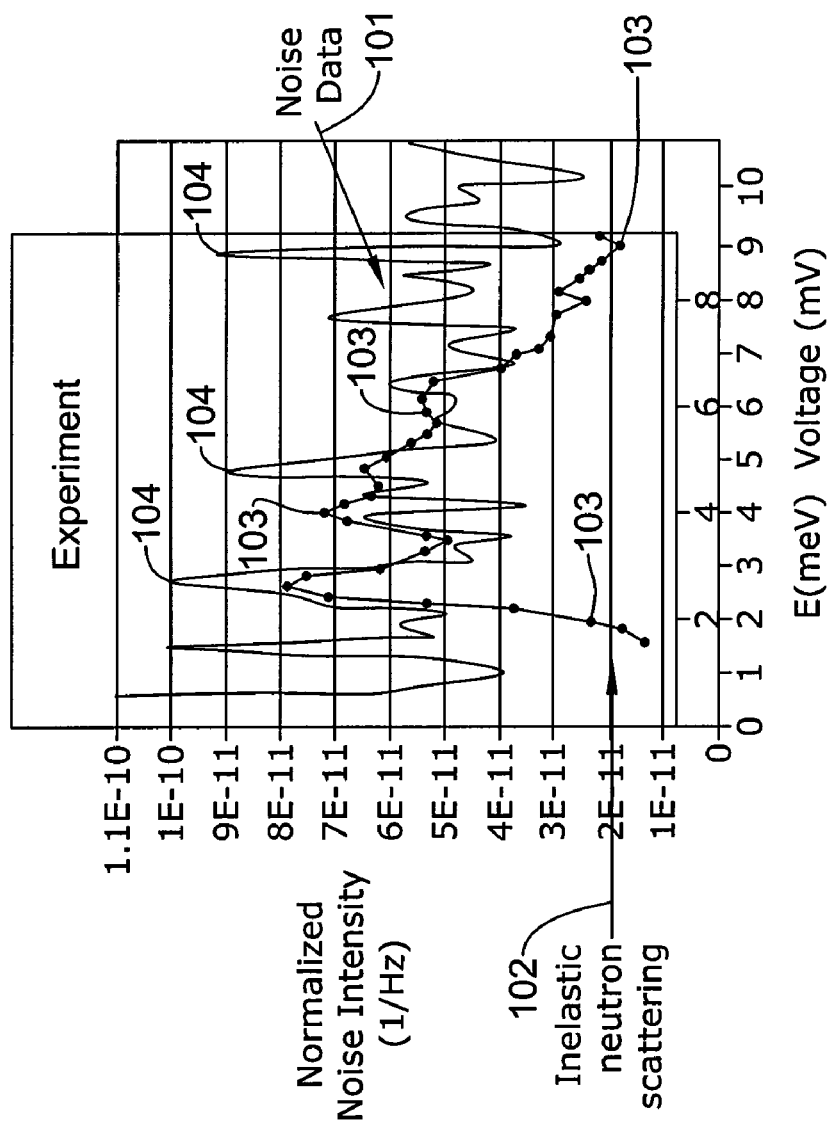
FIG. 10 is a graph showing a comparison between the noise intensity and the external vibration spectrum of C60 for a pulse length of one second.

FIG. 10 is a graph showing a comparison between the noise intensity 101 and the external vibration spectrum 102 of C60 (dots 103) for a pulse length of 1 sec. The noise data 101 presented in this figure were obtained at a frequency of 6 Hz, with a current biasing pulse width of 1 sec, by averaging of 15 snapshot spectra. The noise data 101 were compared with the so-called intermolecular vibration spectrum 102 (or libronic spectrum) of C60 obtained by inelastic neutron scattering (Pintschovius et al., Phys. Rev. Lett. 69, 2662 (1992). The experimental data obtained by inelastic nuclear scattering are shown with dots 103. A good correspondence may be observed between the noise peaks 104 and some C60 vibration lines of very low energy.

Figure 11:
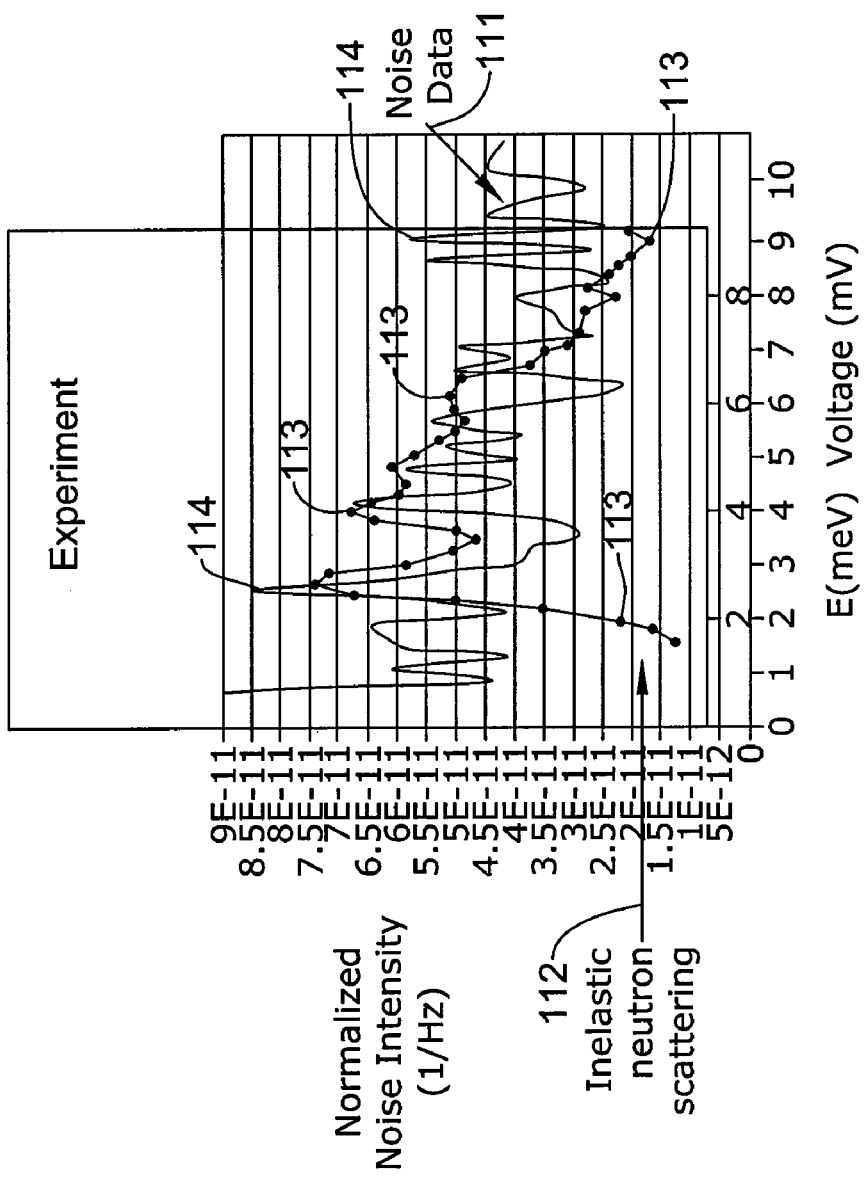
FIG. 11 is a graph showing a comparison between the noise intensity and the external vibration spectrum of C60 for a pulse length of one-half second.

FIG. 11 is a graph showing a comparison between the noise intensity 111 and the external vibration spectrum 112 of C60 (dots 113) obtained by inelastic neutron scattering, for a pulse length of 0.5 sec. The noise data 111 presented in this figure were obtained under the same conditions as those presented in FIG. 10, except for the pulse width which in the case of FIG. 11 was 0.5 sec. The noise structure (e.g., peaks 114) may compare reasonably well with the libronic spectrum 112 of C60. These data support the present approach.

A measurement of very low energy intermolecular vibration modes of molecules may be obtained from the electrical noise of the material. With the electrical noise, sensing molecules located in a conductive matrix may be attained. Other information may be obtained from electrical noise of the material.

In another embodiment, the present approach may be used to investigate materials located in a nanogap such as a few molecules or a single molecule, regardless of their or its nature, respectively. The approach may be used to monitor the modification of the properties of the molecule in the nanogap by physical, chemical or biological methods, approaches and factors, including those aiming at functionalization of the molecule or molecules. Also, the effect of another molecule or other molecules on the molecule in the gap may be investigated and monitored by the present approach.

In review, the present approach of spectroscopy may use an electrical noise measurement to determine the phonon (vibration) spectrum of any conductive material or substance of inorganic or organic nature. It may use an electrical noise measurement to determine bulk, surface or/and interface vibration spectrum (or combinations of these) of any conductive material having the structure of metals, semiconductors, superconductors (in normal state, superconducting state and transition state), liquids, analyte or/and substance of organic and/or inorganic nature. The present approach may use an electrical noise measurement to determine the phonon spectrum of any conductive material resulting from any mechanical, physical or chemical combination of the above materials, in any proportion, including combinations of the same material, regardless of the structure (crystalline, polycrystalline, amorphous, and so on).

The present approach may use an electrical noise measurement to determine the bulk phonon spectrum of any conductive material resulted from any mechanical, physical or chemical combination of the above materials, in any proportion or including combinations of the same material, regardless of the structure (crystalline, polycrystalline, amorphous, and so on). The approach may use an electrical noise measurement to determine the surface vibration spectrum of any conductive material resulted from any mechanical, physical or chemical combination of the above materials, in any proportion or including combinations of the same material, regardless of the structure (crystalline, polycrystalline, amorphous, and so on).

The present approach may use an electrical noise measurement to determine/identify the modification of the vibration spectrum of any conductive material induced by impurities intentionally or nonintentionally introduced in material. The approach may use an electrical noise measurement to determine/identify the modification of the phonon spectrum of any conductive material resulting from any mechanical, physical or chemical combination of the above materials, in any proportion or including combinations of the same material, regardless of the structure (crystalline, polycrystalline, amorphous, and so on).

The present approach may use electrical noise measurement to determine the interface phonon spectrum of any conductive material resulted from any mechanical, physical or chemical combination of the above materials, in any proportion or including combinations of the same material, regardless of the structure (crystalline, polycrystalline, amorphous, and so on).

The approach may use an electrical noise measurement to monitor the phonon spectrum of a material during the processes of impurification of a material with another material. It may use an electrical noise measurement to monitor the phonon spectrum of a material during its synthesis. The approach may use an electrical noise measurement to monitor the phonon spectrum of a material interacting with physical, chemical and biological factor and agents. It may use an electrical noise measurement to monitor the phonon spectrum during the phase transitions. The approach may use an electrical noise measurement to monitor the phonon spectrum of a superconductor during the transition normal-superconducting state or superconducting-normal state.

The present approach may use an electrical noise measurement to measure the surface phonon spectrum. It may use an electrical noise measurement to monitor the modifications of surface phonon spectrum under the influence of any mechanical, physical, chemical and biological agent/factor.

The present approach may use an electrical noise measurement to monitor the phonon spectrum of a surface during the interaction with adsorbates such as molecules, nanoparticles, liquids, liquid droplets, but not limited to these factors only. The approach may use an electrical noise measurement to monitor the phonon spectrum of the surface during its functionalization.

The present approach may use an electrical noise measurement to measure the interface phonon spectrum. It may use an electrical noise measurement to monitor the modifications of interface phonon spectrum under the influence of any mechanical, physical, chemical and biological agent/factor. The approach may use an electrical noise measurement to monitor the phonon spectrum of an interface during the interaction with adsorbates such as molecules, nanoparticles, liquids, liquid droplets, but not limited to these factors only.

The present approach may use an electrical noise measurement to measure the phonon spectrum of a nanoparticle film. It may use an electrical noise measurement to monitor the modification of the phonon spectrum of a nanoparticle film produced by any physical, chemical and/or biological factors or combination of them. The approach may use an electrical noise measurement to monitor the phonon spectrum of a nanoparticle film during the interaction with adsorbates such as molecules, nanoparticles, liquids, liquid droplets, but not limited to these factors only. It may use an electrical noise measurement to monitor the phonon spectrum of a nanoparticle film during its functionalization.

The present approach may use an electrical noise measurement to measure the phonon spectrum of a conducting monolayer. It may use an electrical noise measurement to monitor the modification of the phonon spectrum of a conducting monolayer produced by any physical, chemical and/or biological factors or combination of them. The approach may use an electrical noise measurement to monitor the phonon spectrum of a conducting monolayer during the interaction with adsorbates such as molecules, nanoparticles, liquids, liquid droplets, but not limited to these factors only. It may use an electrical noise measurement to monitor the phonon spectrum of a conducting monolayer during its functionalization.

The present approach may use electrical noise measurement to measure the phonon spectrum of a two-dimensional system of atoms (e.g., graphene). It may use an electrical noise measurement to monitor the modification of the phonon spectrum of a two-dimensional system (e.g., graphene but not only) produced by any physical, chemical and/or biological factors or combination of them. The approach may use an electrical noise measurement to monitor the phonon spectrum of a two-dimensional system of atoms during the interaction with adsorbates such as molecules, nanoparticles, liquids, liquid droplets, but not limited to these factors only.

It may use an electrical noise measurement to monitor the phonon spectrum of a two-dimensional system of atoms during its functionalization. The approach may use an electrical noise measurement to measure the phonon spectrum of a quantum wire, including (carbon) nanotube. It may use an electrical noise measurement to monitor the modification of the phonon spectrum of a quantum wire produced by any physical, chemical and/or biological factors or combination of them.

The present approach may use an electrical noise measurement to measure the phonon spectrum of system (carbon) nanotube-contacts. It may use an electrical noise measurement to monitor the modification of the phonon spectrum of system (carbon) nanotube-contacts produced by any physical, chemical and/or biological agent/factor or combination of them. The approach may use an electrical noise measurement to monitor the phonon spectrum of system (carbon) nanotube-contacts during its functionalization. It may use an electrical noise measurement to monitor the phonon spectrum of system (carbon) nanotube-contacts during interacting with a substrate.

The present approach may use an electrical noise measurement to measure the phonon spectrum of a nanoparticle between two contacts (including a nanogap). It may use an electrical noise measurement to monitor the modification of the phonon spectrum of a nanoparticle between two contacts (including a nanogap) produced by any physical, chemical and/or biological factors or combination of them. The approach may use an electrical noise measurement to monitor the phonon spectrum of a nanoparticle between two contacts (including a nanogap) during its interaction with adsorbates such as molecules, nanoparticles, liquids, liquid droplets, but not limited to these factors only. It may use an electrical noise measurement to monitor the phonon spectrum of a nanoparticle between two contacts (including a nanogap) during its functionalization.

The present approach may use an electrical noise measurement to measure the phonon spectrum of a quantum dot located between two contacts. It may use an electrical noise measurement to monitor the modification of the phonon spectrum of a quantum dot located between two contacts produced by any physical, chemical and/or biological factors or combination of them.

The present approach may measure the vibration spectrum of a molecule located between two contacts (including a nanogap). It may monitor the modification of the vibration spectrum of a molecule located between two contacts (including a nanogap) produced by any physical, chemical and/or biological factors or combination of them. The approach may recognize a material, substance of inorganic or organic nature by comparing the phonon spectrum determined by electrical noise measurement with the phonon spectrum determined by other methods or approaches.

Since the present approach is an electrical method or approach of spectroscopy, in what follows the present approach may be compared with other electrical approaches of spectroscopy, such as IETS and PCS. IETS is an electrical method but, in contrast to the present approach, it may work only at very low temperature. That is because it relies on the principle of electron tunneling which is very ineffective at room temperature. An application of IETS may require a tunneling structure to be prepared. Also, in the IETS, a voltage (V) may be applied and the inelastic events can be observed in the conductance of the tunneling junction. It may be noted that the variation in the conductance is quite weak (one percent); therefore, in many cases, additional calculation of the first (dI/dV) and/or second derivative ($d^2I/dV^2$) may be required to evidence the phonon structure. The structure may occur when the condition $eV=\omega\omega$ is fulfilled (e—elementary charge, V—applied voltage, $\omega$—Planck constant, $\omega$—atomic vibration frequency). This relation may correspond to the electron energy dissipation by inelastic interaction with the lattice phonons. In 1971, Tom Carruthers (Bias-Dependent Structure in Excess Noise in GaAs Schottky Tunnel Junctions, Appl. Phys. Lett., 18, 35 (1971) observed a fine structure (peaks) in the dependence of the noise voltage (mV) on voltage in an Au—GaAs Schottky barrier diode. The measurement was done at a temperature of 4.2° K. One peak was associated with the energy of longitudinal optical phonons in GaAs.

Some extra peaks of electrical measurement were also observed but those have not been identified. These results may be indicative that noise measurements are capable of offering information on the atomic vibration energies in solid and devices. PCS is an electrical approach but, in contrast to the present approach, it may work only at very low temperatures. That is because it relies on the principle of ballistic transport of electrons which appears not effective at room temperature. The application of PCS may require a point contact to be prepared. Also, in the PCS, a voltage may be applied and the inelastic events can be observed in the conductance of the tunneling junction. In another variant, Yanson, Akimenko and Verkin (I. K. Yanson, A. I. Akimenko and A. B. Verkin, Electrical fluctuations in normal metal point-contacts, Solid-St. Commun. 43, 765 (1982)) and Akimenko, Verkin and Yanson (A. I. Akimenko, A. B. Verkin, and I. K. Yanson, Point-Contact Noise Spectroscopy of Phonons in Metals, J. Low Temperature Physics 54, 247 (1984)) measured noise in metallic point contacts. They observed a phonon fine structure in the noise intensity vs. voltage, at a very low temperature (below 4.2° K), in metal point-contacts. The structure may consist of peaks and minima. These authors appeared to correlate the positions of the noise maxima with the emission of the Umklapp (U) phonons, while the position of the minima was correlated with the emission of normal (N) phonons at the Brillouin zone boundaries.

In the present specification, some of the matter may be of a hypothetical or prophetic nature although stated in another manner or tense.

Although the invention has been described with respect to at least one illustrative example, many variations and modifications will become apparent to those skilled in the art upon reading the present specification. It is therefore the intention that the appended claims be interpreted as broadly as possible in view of the prior art to include all such variations and modifications.

What is claimed is:

1. A method of spectroscopy comprising:
   providing a material;
   measuring electrical noise of the material;
   determining information about the material from the electrical noise; and
   determining a second phonon spectrum of the material from a second parameter; and
   wherein:
   the electrical noise is a first parameter;
   the phonon spectrum from the first parameter is a first phonon spectrum; and
   the material is recognized by comparing the first phonon spectrum with the second phonon spectrum.

2. The method of claim 1, wherein the information is a phonon spectrum.

3. The method of claim 1, wherein the information is measurement of very low energy intermolecular vibration modes of molecules.

4. The method of claim 1, further comprising sensing molecules located in a conductive matrix, from the electrical noise.

5. The method of claim 1, further comprising applying a current through the material for providing the electrical noise.

6. The method of claim 1, wherein the phonon spectrum is of a conductive material having an inorganic or organic nature.

7. The method of claim 1, wherein the phonon spectrum is an indication of a vibration spectrum of a molecule.

8. The method of claim 1, wherein the phonon spectrum is a bulk phonon spectrum.

9. The method of claim 1, wherein the phonon spectrum is a surface vibration spectrum.

10. The method of claim 1, wherein a modification of the phonon spectrum of a conductive material is determined from the electrical noise.

11. The method of claim 1, wherein the phonon spectrum is an interface phonon spectrum of the material.

12. The method of claim 1, wherein the phonon spectrum of a material is monitored.

13. The method of claim 1, wherein the material is a nanoparticle.

14. The method of claim 1, wherein the material is a nanoparticle film.

15. The method of claim 1, wherein the material is a two-dimensional system of molecules and/or atoms.

16. The method of claim 1, wherein the material is a system of nanotube contacts.

17. The method of claim 1, wherein the material is a quantum dot.

* * * * *